US00PP10122P

United States Patent [19]

Kleinhanns

[11] Patent Number: Plant 10,122

[45] Date of Patent: Nov. 18, 1997

[54] DAHLIA PLANT NAMED BISUYEL

[75] Inventor: Christoph Kleinhanns, Eisleben, Germany

[73] Assignee: Saatzucht Quedlinburg GmbH, Quedlinburg, Germany

[21] Appl. No.: 660,068

[22] Filed: Jun. 3, 1996

[51] Int. Cl.[6] ..... A01H 5/00

[52] U.S. Cl. ..... Plt./87.8

[58] Field of Search ..... Plt./87.8

*Primary Examiner*—James R. Feyrer
*Assistant Examiner*—Melissa L. Kimball
*Attorney, Agent, or Firm*—C. A. Whealy

[57] ABSTRACT

A distinct cultivar of Dahlia plant named Bisuyel, characterized by its compact growth habit; small leaves and inflorescences that are proportional to the overall plant size; ease of propagation; large inflorescence centers with numerous disc florets; and bright yellow ray florets with darker yellow disc florets.

2 Drawing Sheets

The present invention relates to a new and distinct cultivar of Dahlia plant, botanically known as *Dahlia hybrida*, and hereinafter referred to by the cultivar name Bisuyel.

The new Dahlia is a product of a planned breeding program conducted by the inventor in Quedlinburg, Germany. The objective of the breeding program was to create new Dahlia cultivars having a compact growth habit suitable for 7 to 9-cm container production, small inflorescences, desirable inflorescence colors, and inflorescences and foliage with good substance.

The new Dahlia originated from a cross made by the inventor of the inventor's proprietary Dahlia seedling selections. The cultivar Bisuyel was discovered and selected by the inventor as a flowering plant within the progeny of this cross in a controlled environment in Quedlinburg, Germany.

Asexual reproduction of the new Dahlia by terminal cuttings taken at Quedlinburg, Germany, has shown that the unique features of this new Dahlia are stable and reproduced true to type in successive generations.

The floowing traits have been repeatedly observed and are determined to be the unique characteristics of Bisuyel. These characteristics in combination distinguish Bisuyel as a new and distinct cultivar:

1. Compact growth habit, suitable for 7 to 9-cm containers. Plants do not require growth retardants.
2. Small leaves and inflorescences that are proportional to the overall plant size.
3. Excellent rooting and easy to propagate.
4. Large inflorescence centers with numerous disc florets.
5. Bright yellow ray florets with darker yellow disc florets.

The new Dahlia has not been observed under all possible environmental conditions. The phenotype may vary somewhat with variations in environment such as temperature, daylength and light intensity, without, however, any variance in genotype.

Compared to the female parent, plants of the new Dahlia have smaller inflorescences. Plants of the new Dahlia differ from the male parent in ray floret color.

Plants of the new Dahlia are similar to the cultivar Margaret (disclosed in U.S. Plant Pat. No. 6,769) in ray floret color. However, in side-by-side comparisons conducted in Quedlinburg, Germany, under commercial practice, plants of the new Dahlia differed from plants of the cultivar Margaret in the Following characteristics:

1. Plants of the new Dahlia are more compact and shorter than plants of the cultivar Margaret.
2. Leaves of plants of the new Dahlia are smaller than leaves of plants of the cultivar Margaret.

3. Inflorescences of plants of the new Dahlia are smaller than inflorescences of plants of the cultivar Margaret.

Plants of the new Dahlia are also similar to the cultivar Bayel (U.S. Plant Patent Applied For) in ray floret color. However, in side-by-side comparisons conducted in Quedlinburg, Germany, under commercial practice, plants of the new Dahlia have shorter internodes, longer peduncles, smaller inflorescences, and are taller than plants of the cultivar Bayel.

BRIEF DESCRIPTION OF THE DRAWINGS

The accompanying colored photographs illustrate the overall appearance of the new cultivar, showing the colors as trus as it is reasonably possible to obtain in colored reproductions of this type.

The first photograph comprises a top perspective view of a typical flowering plant of Bisuyel.

The upper photograph on the second sheet of photographs comprises a top perspective view of immature (top) and mature (bottom) leaves. The upper (left) and under (right) sides of the leaves are shown.

The lower photograph comprises a top perspective view of developing inflorescences. From right to left are an opening flower bud, a developing inflorescence, and a fully developed inflorescence. The floret and foliage colors in these photographs appear different than the actual colors due to light reflectance.

In the following description, color references are made to The Royal Horticultural Society Colour Chart except where general terms of ordinary dictionary significance are used. The following observations and measurements describe plants grown in Quedlinburg, Germany, during the winter season under commercial practice in a glass-covered greenhouse with average night temperatures of 15C, average day temperatures of 20C, and light levels of 2,500 lux.

Botanical classification: *Dahlia hybrida* cultivar Bisuyel.
Commercial classification: Pot Dahlia.
Parentage:
- *Male or pollen, parent.*—Proprietary Dahlia seedling selection.
- *Female, or seed, parent.*—Proprietary Dahlia seedling selection.

Propagation:
- *Type.*—Terminal tip cuttings.
- *Time to rooting.*—15 to 20 days with soil temperature of 20C.

*Rooting habit.*—Propagates easily, roots fibrous and well-branched.

Plant description:

*Appearance.*—Perennial herbaceous potted plant. Bushy with stems upright. Freely branching, plants do not require pinching. Compact growth habit and moderate growth rate. Suitable for 7 to 9-cm containers. From a rooted cutting, six weeks are required to produce a flowering pot plant.

*Plant height.*—About 17 cm.

*Stem description.*—Internode length: 1 to 1.5 cm. Diameter: About 3 mm. Color: 144B.

*Foliage description.*—Arrangement: Young foliage: Single. Fully expanded: Compound, trifoliate. Leaf size: Young foliage: Length: About 3 cm. Width: About 2 cm. Mature foliage: Length: About 5 cm. Width: About 3.5 cm. Leaf/leaflet shape: Ovate. Leaf/leaflet apex: Acuminate. Leaf/leaflet base: Attenuate. Leaf/leaflet margin: Slightly serrated. Leaf/leaflet texture: Smooth, glabrous. Petiole length: Young foliage: About 1.5 cm. Fully expanded: About 3 cm. Color: Young foliage upper surface: 137B. Young foliage under surface: 138B/138C. Fully expanded foliage upper surface: 137B. Fully expanded foliage under surface: 138B/138C. Petiole: 144B.

Flowering description:

*Appearance.*—Daisy inflorescence form. Inflorescences borne on termionals above foliage, arising from leaf axils. Disc and ray florets arranged acropetally on a capitulum.

*Flowering response.*—Under natural conditions, plants flower continuous in the summer/autumn in the Northern Hemisphere. At other times of the year, inflorescence initiation and development can be induced under long days/short night conditions (less than 11 hours of darkness). Inflorescences persistent.

*Inflorescence size.*—Diameter: 2.5 to 3 cm. Depth (height): About 1.5 cm.

*Flower bud.*—Shape: Ovoid. Size: Length: About 5 mm. Diameter: About 7 mm. Color: 144B to 151C.

*Ray florets.*—Shape: Oblanceolate. Size: Length: 12 to 15 mm. Width: 5 to 7 mm. Apex: Obtuse. Margin: Entire. Texture: Satiny, smooth and glabrous. Number of ray florets per inflorescence: About 25, two to three rows of florets. Color: Upper surface: 3A. Under surface: 3B.

*Disc florets.*—Number of disc florets per inflorescence: Numerous, about 60. Color: 17B.

*Peduncle.*—Aspect: Erect and strong. Length: 3.5 to 5 cm. Diameter: About 1 mm. Texture: Glabrous. Color: 144B.

*Sepals.*—Quantity per inflorescence: Usually 6 to 8. Shape: Oblanceolate. Tip: Acute. Margin: Entire. Color: 137B.

*Reproductive organs.*—Androecium: Anther size: About 2 mm. Anther color: 17B. Pollen: 17B. Gynoecium: Style length: About 2 mm. Stigma color: 17B.

Disease resistance: No known Dahlia diseases observed to date on plants grown under commercial greenhouse conditions.

Seed production: Seed production has not been observed.

It is claimed:

1. A new and distinct cultivar of Dahlia plant named Bisuyel, as illustrated and described.

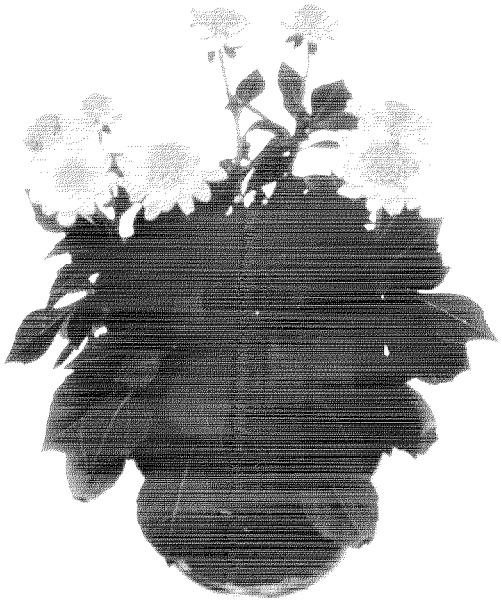

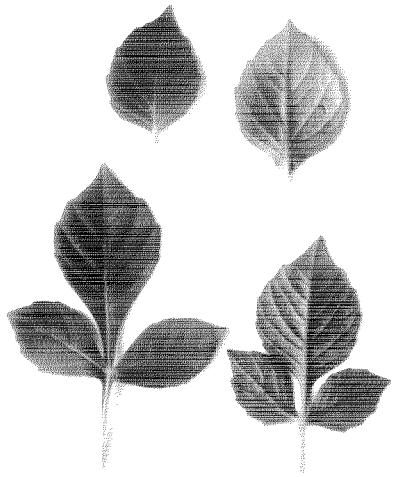
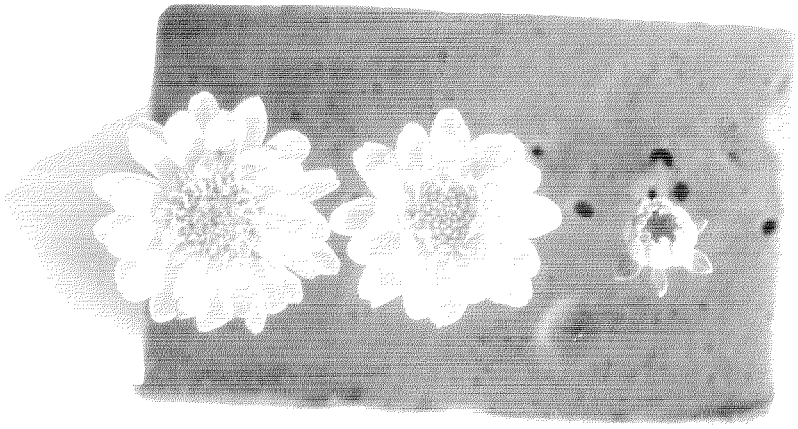

* * * * *